US00PP15377P3

(12) United States Plant Patent
Noodelijk

(10) Patent No.: US PP15,377 P3
(45) Date of Patent: Nov. 30, 2004

(54) ***CHRYSANTHEMUM* PLANT NAMED 'REDOCK ORANGE'**

(50) Latin Name: *Chrysanthemum morifolium*
Varietal Denomination: Redock Orange

(75) Inventor: Robert Noodelijk, Woubrugge (NL)

(73) Assignee: Chrysanthemum Breeders Association, N.V. (NL)

( * ) Notice: Subject to any disclaimer, the term of this patent is extended or adjusted under 35 U.S.C. 154(b) by 130 days.

(21) Appl. No.: 09/910,030

(22) Filed: Jul. 23, 2001

(65) Prior Publication Data

US 2003/0033652 P1 Feb. 13, 2003

(51) Int. Cl.[7] ..... A01H 5/00
(52) U.S. Cl. ..... Plt./296
(58) Field of Search ..... Plt./296

*Primary Examiner*—Anne Marie Grunberg
(74) *Attorney, Agent, or Firm*—Parkhurst & Wendel, L.L.P.

(57) ABSTRACT

A *Chrysanthemum* plant named 'Redock Orange' characterized by its medium sized blooms with orange ray-florets and yellow-green disc florets.

2 Drawing Sheets

RELATED CULTIVARS

'Redock Orange' is related to 'Redock Dark' (pending Ser. No. 09/910,029) and 'Redock Salmon' (pending Ser. No. 09/910,027). These varieties are all mutants of the original 'Redock' (unpatented).

BACKGROUND OF THE INVENTION

'Redock Orange' is a product of a breeding and selection program that had the objective of finding color mutants of 'Redock'. The new plant of the present invention comprises a new and distinct cultivar of *Chrysanthemum* plant that is a natural occuring sport of a parent *Chrysanthemum* named 'Redock' (unpatented). A comparison with parent *Chrysanthemum* 'Redock' is also made in this application. The new cultivar was discovered as a whole plant mutation in September, 1999 by Rob Noodelijk in a controlled environment (greenhouse) in Rijsenhout, Holland. The first act of asexual reproduction of 'Redock Orange' was accomplished when vegetative cuttings were taken from the initial selection in November 1999 in Rijsenhout, Holland.

SUMMARY OF THE INVENTION

The present invention is a new and distinct variety of *Chrysanthemum* bearing medium sized blooms with orange ray-florets and yellow-green disc florets.

BRIEF DESCRIPTION OF THE DRAWINGS

The present invention of a new and distinct variety of *Chrysanthemum* is shown in the accompanying drawings, the color being as nearly true as possible with color photographs of this type.

DESCRIPTION OF THE INVENTION

Figure 1:
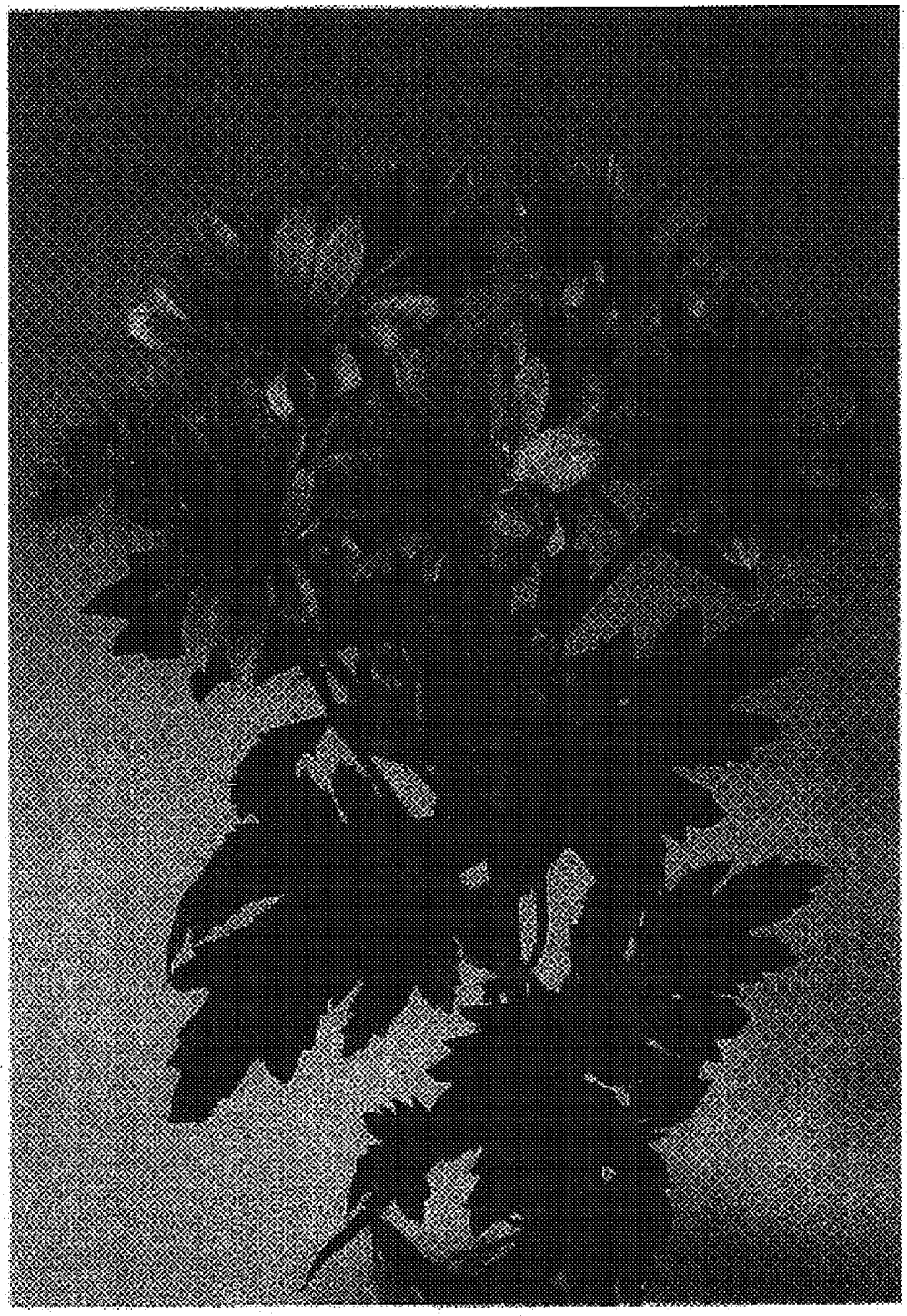
FIG. 1 shows a plant of the cultivar in full bloom.
Figure 2:
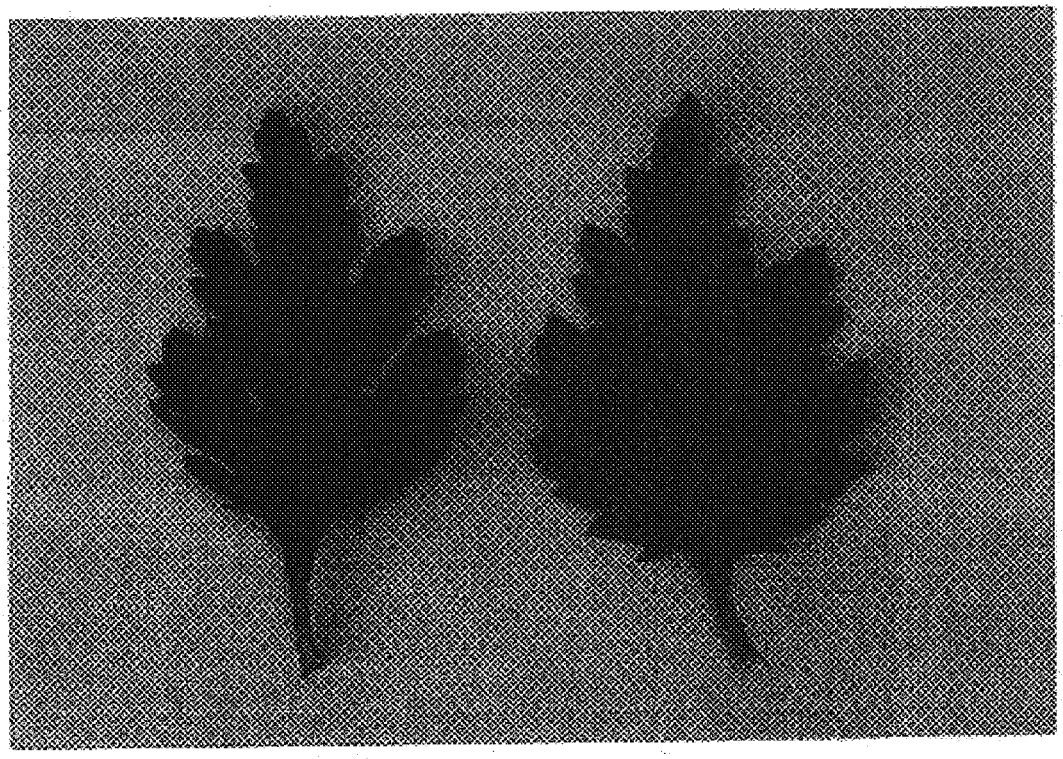
FIG. 2 shows the foliage of the cultivar.

This new variety of *Chrysanthemum* is of the botanical classification *Chrysanthemum morifolium*. The observations and measurements were gathered from plants grown in April/May in a greenhouse in Rijsenhout, Holland in a photo-periodic controlled crop under conditions generally used in commercial practice. The greenhouse temperatures during this crop were at day-time between 18° C. and 25° C. and at night 20° C. After a long day period of 14 days, the photo-periodic response time in this crop was 47 days. After the long day period to flowering, growth retardants were applied 3 times in an average dose of 2.5 gram/liter water. No tests were done on disease or insect resistance or susceptibility. This new variety produces medium sized blooms with orange ray-florets and yellow-green disc-florets blooming on the plant for 4 weeks. This new variety of *Chrysanthemum* has been found to retain its distinctive characteristics throughout successive propagations; however, the phenotype may vary significantly with variations in environment such as light intensity and temperature. To show the phenotype as described 'Redock Orange' can be planted without assimilation lightning (high pressure sodium lamps) between week 50 and week 40 of the next year under greenhouse conditions in Holland. With assimilation light (minimum level 2500 lux) it can be planted year round under greenhouse conditions in Holland.

From the cultivars known to inventor the most similar existing cultivar in comparison to 'Redock Orange' is 'Redock'. When 'Redock' and 'Redock Orange' are being compared the following differences and similarities are noticed. The difference of 'Redock' and 'Redock Orange' is the orange ray-floret color for which characteristics 'Redock Orange' has been selected out of 'Redock'. All other characteristics of 'Redock' and 'Redock Orange' are similar. From other commercial varieties 'Orange Reagan' (U.S. Plant Pat. No. 8,769) and 'Orange Elite Reagan' are the most similar. The differences between 'Orange Reagan', 'Orange Elite Reagan' and 'Redock Orange' are (1) Flower form and color. The ray-florets of 'Redock Orange' are more upright, less broad, more pointed and more concave. (2) Vigour. Under the same circumstances the plants of 'Redock Orange' are 20 cm longer. (3) Response time. The response time of 'Redock Orange' is shorter. (4) The disc-floret size of 'Redock Orange' is smaller. (5) Foliage size and color. The foliage of 'Redock Orange' is bigger and more yellow-green.

The following is a description of the plant and characteristics that distinguish 'Redock Orange' as a new and distinct variety. The color designations are taken from the plant itself. Accordingly, any discrepancies between the color designations and the colors depicted in the photographs are due to photographic tolerances. The color chart used in this description is: The Royal Horticultural Society Colour Chart, 1995 edition.

TABLE 1

| Botanical Description of CULTIVAR 'Redock Orange' | |
|---|---|
| Bud | |
| Size | Small, cross-section 0.7 cm height 0.9 cm |
| Outside color | Greyed-orange 170 C |
| Involucral bracts | 3 rows, length 8 mm, width 3 mm |
| Involucral bracts among disc-florets | Not present |
| Involucral bracts color | Green 147 B |
| Bloom | |
| Type | Single |
| Height | High |
| Size | Medium |
| Fully expanded | 7.0 cm |
| Number of blooms per single stem | Average of 14 |
| Seeds | Not produced |
| Performance (blooming period) | 4 weeks |
| Fragrance | Typical *chrysanthemum* |
| Color | |
| Center of the flower (disc-florets) | Immature yellow-green 144 A<br>Mature yellow-green 151 C |
| Color of upper surface of the majority of the ray-florets | Orange 26 B |
| Color of the lower surface of the majority of the ray-florets | Yellow-orange 16 B |
| Tonality from distance | A spray mum with orange flowers and a yellow-green disc |
| Discoloration to color | To color yellow-orange 16 A |
| Ray florets | |
| Texture | Upper and under side smooth |
| Number | 26–28 |
| Cross-section | Strongly concave |
| Longitudinal axis of majority | Reflexing |
| Length of corolla tube | Short |
| Ray-floret length | 3.3 cm |
| Ray-floret width | 1.0 cm |
| Ratio length/width | Medium |
| Shape of tip | Pointed, very occasionally round |
| Disc florets | |
| Disc diameter | 0.8–1.0 cm |
| Distribution of disc florets | Numerous, clearly visible at all stages of flowering |
| Shape | Tubular |
| Color | Yellow-green 144 A |
| Receptacle shape | Conical raised |
| Reproductive Organs | |
| Stamen (present in disc florets only) | Thin 3 mm in length |
| Stamen color | Yellow-green 144 B |
| Pollen | No pollen present |
| Pollen color | Not applicable |
| Styles (present in both ray and disc florets) | Thin |
| Style color | Yellow-green 144 B |
| Style length | 4 mm |
| Stigma color | Yellow-green 144 B |
| Stigma width | 2 mm |
| Ovaries | Enclosed in calyx |

TABLE 1-continued

| Botanical Description of CULTIVAR 'Redock Orange' | |
|---|---|
| Plant | |
| Form | A spray mum meant for erect culture |
| Growth habit | Upright |
| Growth rate | Very vigorous |
| Height | 125–135 cm |
| Internodes | 2.5–3.0 cm |
| Spray formation | Corymbiform |
| Stem color | Yellow-green 147 B |
| Stem strength | Medium |
| Stem brittleness | Present |
| Stem anthocyanin coloration | Absent |
| Peduncle length | Near the top 16 cm, near the middle 23 cm, near the bottom 28 cm |
| Peduncle color | Green 147 B |
| Peduncle, attachment | Brittle |
| Peduncle, angle with stem | Small, 30° C. |
| Flowering response (photo-periodic controlled crop, not natural season) | 47 days |
| Foliage | |
| Color | Upper side yellow-green 147 A<br>Under side green 138 B |
| Size | large; length 12.0–14.0 cm width 7.0–8.0 cm |
| Quantity (number per single stem) | 30–34 |
| Shape | Ovate and deeply lobed |
| Texture upper side | Fleshy and glabrous |
| Texture under side | Pubescent |
| Ribs and veins upper side | Ribs and veins well developed |
| Ribs and veins under side | Ribs and veins well developed |
| Venation arrangement | Palmate |
| Shape of the margin | Lobed |
| Shape of base of sinus between lateral lobes | Round |
| Margin of sinus between lateral lobes | Converging |
| Shape of base | Rounded |
| Apex | Mucronate |

TABLE 2

| Differences with the comparison Varieties | | | | |
|---|---|---|---|---|
| | 'Redock Orange' | 'Redock' | 'Orange Reagan' | 'Orange Elite Reagan' |
| Ray-floret color | Orange 26 B | Purple 75 C | Greyed-Orange 169 A | Yellow-Orange 20 B |
| Flower height | High | High | Low | Low |
| Cross-section of ray-floret | Strongly concave | Strongly concave | Flat | Flat |
| Vigour | Very vigorous | Very vigorous | Vigorous | Vigorous |
| Plant height | 125–135 cm | 125–135 cm | 100–125 cm | 105–130 cm |

I claim:

1. A new and distinct variety of *Chrysanthemum* plant as described and illustrated.

* * * * *